US012716859B2

(12) United States Patent
Mahshid et al.

(10) Patent No.: US 12,716,859 B2
(45) Date of Patent: Aug. 25, 2026

(54) ELECTROCHEMICAL IMMUNO-BIOSENSOR AND METHOD FOR DETECTION OF CIRCULATING PROTEIN BIOMARKERS

(71) Applicant: SUNNYBROOK RESEARCH INSTITUTE, Toronto (CA)

(72) Inventors: Sahar S. Mahshid, Toronto (CA); Alain Dabdoub, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 522 days.

(21) Appl. No.: 18/014,227

(22) PCT Filed: Jun. 22, 2021

(86) PCT No.: PCT/CA2021/050859

§ 371 (c)(1),
(2) Date: Jan. 3, 2023

(87) PCT Pub. No.: WO2022/000073

PCT Pub. Date: Jan. 6, 2022

(65) Prior Publication Data

US 2023/0258596 A1 Aug. 17, 2023

Related U.S. Application Data

(60) Provisional application No. 63/047,994, filed on Jul. 3, 2020.

(51) Int. Cl.
*G01N 27/327* (2006.01)
*C07K 16/28* (2006.01)

(52) U.S. Cl.
CPC ......... *G01N 27/3277* (2013.01); *C07K 16/28* (2013.01)

(58) Field of Classification Search
CPC . G01N 27/3275; G01N 27/3277; C07K 16/28
See application file for complete search history.

(56) References Cited

U.S. PATENT DOCUMENTS

2016/0238617 A1 8/2016 Parham
2017/0045503 A1* 2/2017 Vallée-Bélisle ...... G01N 33/542
2018/0106791 A1 4/2018 Gordon

FOREIGN PATENT DOCUMENTS

WO 2019203493 A1 10/2019

OTHER PUBLICATIONS

Luna, High-Curvature Nanostructuring Enhances Probe Display for Biomolecular Detection, Nano Letters 2017, 17, pp. 1289-1295. (Year: 2017).*

(Continued)

*Primary Examiner* — C. Sun
(74) *Attorney, Agent, or Firm* — HILL & SCHUMACHER

(57) ABSTRACT

The present disclosure provides a biosensor platform for rapid detection of otolin-1 and prestin, blood-circulating proteins specifically expressed in the vestibule and cochlea, respectively. The platform is designed on a DNA-based immunoassay that employs conjugated antibodies for target protein recognition, which when bound, altered the DNA-DNA hybridization on the surface, resulting in generation of a concentration-dependent electrochemical output in whole blood. Signal amplification is acquired by employing high-curvature nanostructured electrodes for sensitive sample analysis at low picomolar concentrations with a three-fold quantitative range, in a 10-μL sample in 10 minutes. Using antibodies as recognition elements allows for the adaptation of this platform to detect any blood-circulating protein.

19 Claims, 6 Drawing Sheets

(56) References Cited

OTHER PUBLICATIONS

Mahshid, Biomolecular Steric Hindrance Effects Are Enhanced on Nanostructured Microelectrodes, Analytical Chemistry, 2017, vol. 89, pp. 9751-9757. (Year: 2017).*
S.S. Mahshid, Peptide-Mediated Electrochemical Steric Hindrance Assay for One-Step Detection of HIV Antibodies, Analytical Chemistry, 2019(91), pp. 4943-4947; the supplemental information is included (Year: 2019).*
"Deafness and hearing loss", World Health Organization, https://www.who.int/news-room/fact-sheets/detail/deafness-and-hearing-loss#:~:text=People%20who%20are%20hard%20of,use%20sign%20language%20for%20communication, Mar. 1, 2020, 6 pages.
Government of Canada, "The Cost of Injury in Canada", https://www.canada.ca!en!public-health!services!injury-prevention!cost-injury-canada.html, Apr. 15, 2020, 3 pages.
Naples, J., et al., "Prestin as an otologic biomarker of cisplatin ototoxicity in a guinea pig model", Otolaryngology-Head and Neck Surgery, 2018. 158(3): p. 541-546.
Parham, K. and J. Dyhrfjeld-Johnsen, "Outer hair cell molecular protein, prestin, as a serum biomarker for hearing loss: proof of concept", Otology & Neurotology, 2016. 37(9): p. 1217-1222.
Hana, R.S. and B.L. Bawi, "Prestin, otolin-1 regulation, and human 8-oxoG DNA glycosylase 1 gene polymorphisms in noise-induced hearing loss", Ibnosina Journal of Medicine and Biomedical Sciences, 2018. 10(2): p. 60, 5 pages.
Mio, K., et al., "The motor protein prestin is a bullet-shaped molecule with inner cavities", Journal of Biological Chemistry, 2008. 283(2): p. 1137-1145.
Deans, M.R., J.M. Peterson, and G.W. Wong, "Mammalian Otolin: a multimeric glycoprotein specific to the inner ear that interacts with otoconial matrix protein Otoconin-90 and Cerebellin-1", PloS one, 2010. 5(9): p. e12765, 15 pages.
Dogan, M., M. Sahin, and V. Kurtulmus, "Otolin-1, as a Potential Marker for Inner Ear Trauma after Mastoidectomy", The journal of international advanced otology, 15(2), 2019, 4 pages.
Parham, K., et al., "Inner ear protein as a biomarker in circulation?", Otolaryngology—Head and Neck Surgery, 2014. 151(6): p. 1038-1040.
Sahar Sadat Mahshid, et. al., "A Highly Selective Electrochemical DNA-Based Sensor That Employs Steric Hindrance Effects to Detect Proteins Directly in Whole Blood", Journal of American Chemical Society, 137 (2015), 15596-15599.
Sahar Sadat Mahshid, et. al., "Peptide-Mediated Steric Hindrance Hybridization Assay for HIV Antibodies", Anal. Chem., 91, 2019, 8, 4943-4947.
Mahsa Jalali, Tamer Abdel Salam, Sahar Sadat Mahshid, et. al. "A Hierarchical 3D Nanostructured Microfluidic Device for Sensitive Detection of Pathogenic Bacteria", Small, 2018, 1801893, 15 pages.
Sahar Sadat Mahshid, et. al., "Biomolecular Steric Hindrance Effects Are Enhanced on Nanostructured Microelectrodes", Analytical Chemistry, 89, 2017, 9751-9757.
Sahar Sadat Mahshid, et. al., "An Electrochemical DNA-based Immunoassay that Employs Steric Hindrance to Detect Small Molecules Directly in Whole Blood", ACS Sensors, 2 (2017), 718-723.
Wendi Zhou, Sahar Sadat Mahshid, et. al., "Steric Hindrance Assay for Secreted Factors in Stem Cell Culture", ACS Sensors, 2 (2017), 495-500.
International Search Report for PCT/CA2021/050859 dated Sep. 24, 2021, 4 pages.
De Luna, Phil, et al., "High-Curvature Nanostructuring Enhances Probe Display for Biomolecular Detection", American Chemical Society, Nano Letters, Feb. 8, 2017 (Feb. 8, 2017), vol. 17(2), pp. 1289-1295, [online] retrieved on Aug. 31, 2021 (Aug. 31, 2021)], Retrieved from the Internet: https://doi.org/10.1021/acs.nanolett.6b05153.
Mahshid, Sara, et al., "Mechanistic Control of the Growth of Three-Dimensional Gold Sensors". American Chemical Society, The Journal of Physical Chemistry C, Sep. 22, 2016 (Sep. 22, 2016), vol. 120(37), pp. 21123-21132, [online] [retrieved on Aug. 31, 2021 (Aug. 31, 2021)]. Retrieved from the Internet https://doi.org/10.1021/acs.ipcc.6b05158.

* cited by examiner

ELECTROCHEMICAL IMMUNO-BIOSENSOR AND METHOD FOR DETECTION OF CIRCULATING PROTEIN BIOMARKERS

FIELD

The present disclosure relates to an electrochemical immuno-biosensor for the detection of blood circulating protein biomarkers indicative of various diseases or conditions. More particularly the present method and sensor system relates to the detection of otolin-1 and prestin proteins, which are circulating biomarkers of the inner ear.

BACKGROUND

In the past two decades, rapid point-of-care diagnostic approaches based on the detection of biomarkers have been penetrating in many areas of medical diagnostics including infectious diseases[1,2], cancers[3], and neurological disorders[4,5], but not yet inner ear diseases. In fact, current methods to measure inner ear function utilize a set of physical and neurological examinations such as audiograms[6] (for hearing thresholds), vestibular evoked myo-genic potentials[7] (for vestibular function), or posturography[8] (for balance evaluations), which do not indicate the specific sites of degeneration within the inner ear[9].

Permanent damage to the cellular sites of the inner ear—sensory hair cells, neurons, synapses, or stria vascularis—due to noise exposure, aging, and side effect of antibiotics (aminoglycosides) or chemotherapeutic drugs (cisplatin) can result in hearing loss or vestibular disorders[10,11], which can only be identified post mortem. This leads clinicians to adopt a one-size-fits-all approach to the treatment, as they are not equipped with the information required to apply targeted treatment or rehabilitation for the specific injury. As new strategies based on gene and stem cell therapies are being developed[12-16], there is an unmet need for the development of novel diagnostic approaches based on the detection of inner ear effective biomarkers circulating in the blood, to be able to identify the sites of cellular damage resulting in more precise diagnostics to ultimately guide therapy.

The lack of knowledge about inner ear specific biomarkers has been a main challenge toward the development of such advancements. However, recent studies have shown the alteration of a number of serum proteins in human and animal models as indicators of inner ear disorders[17-20]. Otolin-1 is a scaffolding protein expressed in the utricle and saccule—the otolith organs which are part of the vestibular component of the inner ear[21], and prestin is a motor protein uniquely expressed in the cochlea, particularly in outer hair cells[22,23] Changes in serum otolin-1 levels are detectable in patients with balance/vestibular end organ problems such as benign paroxysmal positional vertigo[24]. Furthermore, in an animal-ototoxicity model, changes in prestin blood levels were detectable before any shifts in audiometric thresholds could be traced[25], indicating the ability of the two proteins to perform as potential biomarkers for inner ear blood-based diagnosis.

Recently, approaches for rapid point-of-care detection of macromolecules, particularly proteins, for disease diagnostics have been developed with the aim of reducing the time and limit of detection compared to currently available multiple-step detection processes (e.g., Enzyme-Linked Immunosorbent Assay (ELISA[26]) and Western blots[27])[28-30]. Among platforms based on optical or mass detection, electrochemical biosensors, in principle, provide selectivity for capturing target molecules while delivering a specific measurable signal[31,32] However, achieving high levels of sensitivity and selectivity in whole blood remains challenging. In this case, various recognition strategies are proposed utilizing antibodies, proteins, synthetic deoxyribonucleic acids (DNAs), and small-molecules interactions with the target of interest[33-37]. Furthermore, the sensor's surface, when combined with nanostructured electrodes, offers a large surface area in small sample volumes[38], and enhancement in the molecular capturing mechanism on the limited geometry of the surface[39], resulting in the improvement of the sensitivity and detection limit of electrochemical biosensors[40].

SUMMARY

The present disclosure provides a biosensor platform utilizing a DNA-based immunoassay immobilized on nanostructured electrodes for the detection of otolin-1 and prestin proteins, which are potential biomarkers of balance and hearing disorders, respectively. Taking advantage of the steric hindrance mechanism[41] on the nanostructured electrodes[42], the present inventors have designed a recognition strategy adapting the conjugated antibodies that can be extended further to a variety of different target proteins by incorporating their specific antibodies. The electrochemical biosensor can potentially overcome the challenges toward one-step rapid detection at the point-of-care.

The present inventors have developed the first biosensor for inner ear biomarkers. The electrochemical biosensor is analogous to commercially available glucose-meter (for measuring blood glucose in diabetic patients) for the direct non-invasive detection of otolin-1 and prestin, two blood-circulating protein biomarkers specifically expressed in the balance organs (utricle and saccule) and cochlea of the inner ear, respectively. The platform is designed based on two advances in nanobiotechnology to improve the functionality of the sensor toward one-step protein detection in complex media (e.g. whole blood). (1) A DNA-based immunoassay employs, first, interactions of oligonucleotide sequences to specify the sensors electrochemical signal when deployed in complex media; second, conjugated antibodies for target protein recognition, which when bound alters the DNA-DNA hybridization on the surface with the steric effects resulting in the generation of the concentration-dependent electrochemical signal output. (2) The high-curvature nanostructured electrode is used for signal amplification to enable sensitive sample analysis at low picomolar concentrations with a three-fold quantitative range, as well as to acquire the analysis in a low 10 μM (micromolar) sample volume in under 30 minutes (min).

The synthetic assay utilizes a high population of short single-strand capturing DNA probes immobilized on the surface of gold nanostructure electrodes deposited on glass chips with addressable electrodes. The signaling DNA probes, which are mixed with the target sample before being added on the sensor surface, are designed to carry and place the redox moiety, methylene blue (MB), on the sensing surface and generate an electrochemical current signal upon hybridization. On the other extremity, the signaling DNA probes are attached to the antibody recognition element utilizing a streptavidin-biotin interaction. The recognition strategy disclosed herein is unique as it offers a universal detection mechanism knowing the high-affinity-interaction of streptavidin-biotin ($K_D$=40 fM) and the ability to incorporate different antibodies specific to various targets. The steric effects of such a recognition molecule on the surface hybridization can be extensively diminished within the curvatures of surface nanostructuring. When the target protein is bound to the recognition element on the signaling DNA probe, the steric hindrance of the target protein limits the more significant number of successful hybridizations to the surface resulting in an elevated reduction of the current signal.

There is provided an electrochemical immuno-biosensor-based method for detecting blood circulating target protein biomarker, comprising:

- selecting a target protein biomarker to be detected for;
- identifying an antibody complimentary to the target protein biomarker;
- preparing a recognition complex of antibody with streptavidin (1:1)thereby preparing a streptavidin-conjugated-antibody recognition complex;
- mixing the recognition complex with signaling DNA probes to produce a final recognition complex comprising signaling probe plus streptavidin-conjugated-antibody complex, the signaling DNA probes being complexed with a redox moiety;
- preparing a mixture of the final recognition complex with a sample being tested for the presence of the target protein biomarker such that any target proteins present in the sample bind with the antibody of the final recognition complex;
- preparing high curvature gold nanostructure working electrode and immobilizing capturing DNA probes onto a surface of the gold nanostructure electrode and adding the mixture of final recognition complex with a sample to the surface of the working electrode to the mixture of the sample and final recognition complex; and
- performing square wave voltammetry (SWV) on the sample and plotting the current versus voltage and comparing the sample current versus voltage plots to current versus voltage plots obtained using a calibration solution not containing any target protein biomarker and based on differences between the sample and calibration current versus voltage plots determining the presence or absence of the target protein biomarker.

The step of mixing the recognition complex with signaling DNA probes to produce a final recognition complex may comprise the signaling DNA probe being added to the mixture (5:1) and (10:1) to make a final recognition solution of 25 nM signaling probe+5 nM (nanomolar) streptavidin-conjugated-antibody and 10 nM signaling probe+100 pM (picomolar) streptavidin-conjugated-antibody, respectively.

The signaling DNA probes are bound to the final recognition complex utilizing a streptavidin-biotin interaction.

The signaling DNA probes are shorter and complementary to the capturing DNA probes, which upon hybridization, bring the redox moiety, to the surface and generate the current signal.

The redox moiety may be methylene blue (MB), or any other organic or inorganic molecules that can be attached to the probes and generate redox activity upon applying proper voltage.

The target protein being detected may be otolin-1, so that the antibody is anti-otolin-1 antibody.

The target protein being detected may be otolin-1 in a blood sample, and wherein the antibody can be replaced with the antibody Fab fragment or a peptide-derivate of otolin-1 protein, or replace with the otolin-1 protein or otolin-1 protein antigen for indirect detection of target otolin-1, in a competition assay.

The target protein being detected may be prestin, and wherein the antibody is anti-prestin antibody.

The target protein being detected may be prestin in a blood sample, and wherein the antibody can be replaced with a peptide-derivate of prestin protein or antibody Fab fragment, or replaced with the prestin protein or prestin protein antigen for indirect detection of target prestin, in a competition assay.

The target protein being detected may be prestin in a blood sample, and wherein the antibody may be prestin protein or a peptide-derivate of prestin protein for indirect detection of target prestin, in a competition assay.

The sample may be human blood.

The sample may be human biofluid, including serum, plasma, saliva, nasopharyngeal, urine, perilymph, and any other liquid-based biofluid.

The sample may be animal biofluid including blood.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the accompanying drawings, in which:

FIGS. 1A to 1C shows a schematic illustration and proof of principle for the immunosensor developed on nanostructures, in which:

FIG. 1A shows a 20-lead chip having 200 μm nanostructures electrodeposited (top) on the 10 μm-apertures (bottom) of addressable electrodes. The immunoassay is having a layer of capturing probes immobilized on the surface of nanostructures.

FIG. 1B shows when no attachment to target proteins (panel B') and when attached, (panel B"). When not attached to the target proteins (panel B',top), the current signal from hybridization of signaling probes carrying the recognition-antibodies is relatively high (without target). Upon binding to the target protein (B", bottom), the steric hindrance of target proteins will reduce the number of successful hybridizations to the surface and consequently suppress the current signal (with target) to give the lower current signal compared to the higher current plot obtained without the target proteins present.

FIG. 1C shows sensor performance in PBS buffer (panel C') and in whole blood (panel C"). The sensor's performance was tested and confirmed the same in PBS buffer (panel C') and in whole blood (panel C") by comparing the signal gain reduction at 10 nM (34% vs 33%) and 20 nM (64% vs 67%) of otolin-1 (OTOL1) and 20 nM (77% vs 78%) of prestin (PRES). Sample media: PBS 1× 10 mM $MgCl_2$ buffer, and 100% human whole blood; recognition compound: 5 nM of streptavidin-conjugated antibody previously bound to 25 nM of signaling probes; chips were divided into two zones with a hydrophobic line, each zone loaded with 10 μL of target solution for 10 min-incubation, kept in humid chamber; ** $P<0.0001$,  $P<0.01$ significance versus concentrations.

DETAILED DESCRIPTION

Figure 1A:
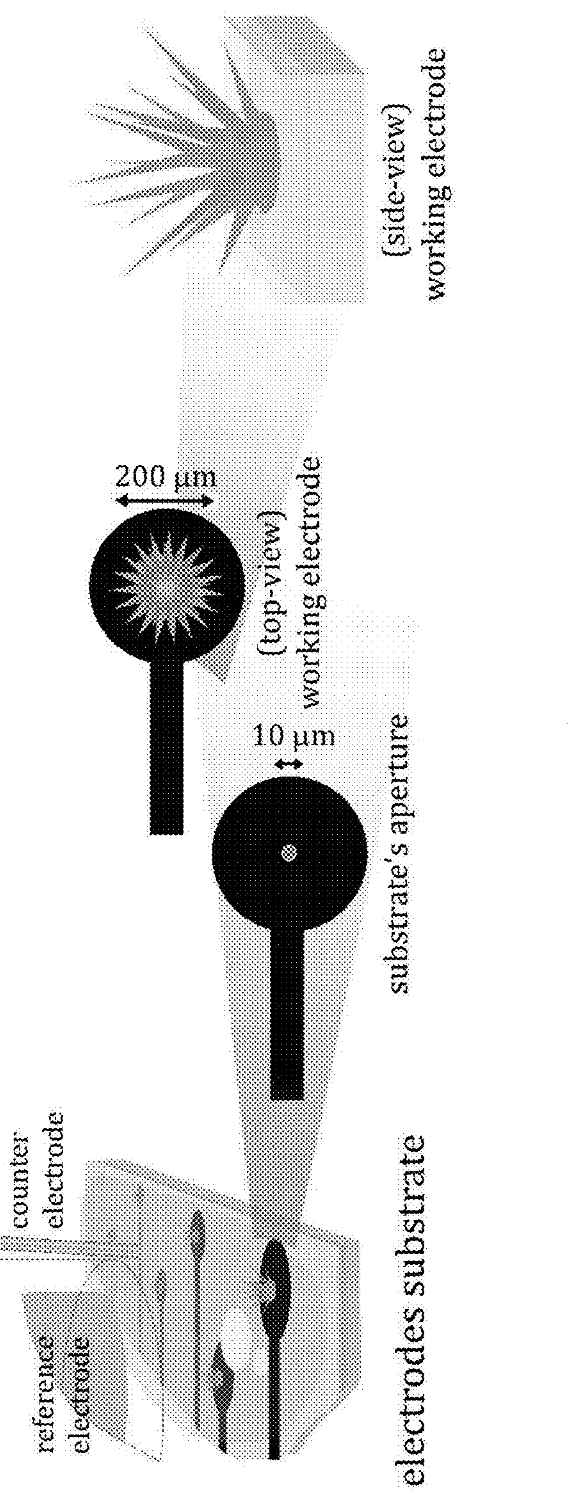

Various embodiments and aspects of the deep orbital access retractor device disclosed herein will be described with reference to details discussed below. The following description and drawings are illustrative of the disclosure and are not to be construed as limiting the disclosure. The figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein, the terms "generally" and "essentially" are meant to refer to the general overall physical and geometric appearance of a feature and should not be construed as preferred or advantageous over other configurations disclosed herein.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein, the phrase "high-curvature nanostructured electrode(s)" refers to a structure that consists of thousands of nano-needles with sharp tips that are located in close proximity representing a tree-like/spiky-like/shrub-like structure in microscales (e.g., about 1 to about 300 μm). They can be compared with low curvature nanostructures where the structure contains round-shape tips such as nanoparticles and/or nanorods. The bigger the size of the structure (within about 1 to about 300 micrometers (μm)) is, the more the number of branches and nano-needles are generated, as well as more sites for probe immobilization. It has been shown that immobilized probes are displayed at a high deflection angle on these branches resulting in suppression of the probe aggregation among adjacent probes allowing greater accessibility and more efficient attachment of the target molecules to the surface, which can tremendously improve the sensitivity of the sensor.

As used herein the phrase "target protein" refers to the protein that is indicative of the disease being tested for which is known to circulate in blood.

As used herein, the term "antibody" refers to a blood protein produced in response to and counteracting the target protein (antigen). Antibodies combine chemically with substances which the antibody recognizes as alien, such as bacteria, viruses, and foreign substances in the blood.

As used herein, the phrase "recognition complex" refers to the molecular complex which "recognizes" and forms a complex with the target protein. In this disclosure the recognition complex comprises streptavidin conjugated with the antibody being used to detect the selected protein, thus giving a streptavidin-conjugated-antibody complex.

As used herein, the phrases "capturing DNA probes" or "capturing probes" refers to single-strand capturing DNA probes or DNA-analog probes (e.g., peptide nucleic acid (PNA) strands) immobilized on the surface of the gold nanostructure electrodes.

As used herein the phrase "signaling DNA probes" refers to DNA strands or DNA-analog strands (e.g., PNA strands) designed to carry and place a redox moiety on the sensing surface and generate an electrochemical current signal upon hybridization. The signaling DNA probes are attached to the antibody recognition element utilizing a streptavidin-biotin interaction. The signaling DNA probes are shorter and complementary to the capturing DNA probes (or strands), which upon hybridization, bring the redox moiety, to the surface and generate the current signal. The redox moiety (or redox label, or redox indicator) may be methylene blue (MB), or any other organic or inorganic molecules that can be attached to the probes and generate redox activity upon applying proper voltage.

Several DNA probe immobilization techniques have been employed in electrochemical DNA sensing for immobilized or captured DNA probes on the electrode surface, such as adsorption methods, covalent bonding and avidinbiotin interaction.

The adsorption methods include physical adsorption and electrochemical adsorption. In physical adsorption or physisorption, forces of attraction are due to Van der Waals' forces between the solid surface and the bio-molecule and the quantity binding to the surface depends on surface properties including temperature, pressure and the surface roughness. In electrochemical adsorption, forces of attraction between the surface and DNA are due to ion-to-ion interactions between the negatively charged DNA and the positively charged surface. By applying a constant positive potential (e.g., 0.8 Volts (V)), the phosphate group of the DNA molecule binds to the positively charged surface due to electrostatic attraction. In both techniques, the immobilized electrodes can be washed with distilled water to remove loosely adsorbed DNA and dried under nitrogen gas. However, the DNA adsorption immobilization method results in orientation of the molecules parallel to, rather than perpendicular to the surface where the DNA backbone is attached to the surface and base pairing sites exposed to the liquid. This configuration is not ideal for the present design of assay on the surface which relies on the spatial orientation of DNA probes standing on the surface to hybridize to the target molecule[43,44].

The covalent immobilization of DNA on the surface has some advantages when compared to adsorption method mainly because the DNA probes are bound to the electrode surface by one end only, which provides more structural flexibility and increases the accessibility for more efficient hybridization. The covalent binding of DNA probes to the surface is based on a modification on the surface to provide some active groups in the electrode material such as carboxylic or amino groups. The active group on the electrode surface is in charge of interacting with the DNA probe through either the guanine or one of the ends (5 or 3) of DNA. Covalent immobilization provides a stable detection layer preventing the desorption of DNA probe from the electrode unlike the adsorption technique[45].

The immobilization method based on interactions between biomolecules such as avidin-biotin complex formation is more secured by the affinity strength of the interactions. In this case, the surface is modified to carry avidin molecules as binding points for the biotinylated-DNA probes (the DNA probes can be modified with biotin on either 5' or 3' ends) to be immobilized on the surface[46].

Herein, the method and system rely upon a property of gold electrodes that can generate a strong binding to the thiol (—SH) to form the self-assembly monolayer of DNA probe on the surface. In this case, the DNA probe is modified with a thiol on the 5' end, which upon activation with TCEP (Tris(2-carboxyethyl) phosphine hydrochloride) can directly bind to the surface of gold electrode without further modification on the surface. The density of the probes on the surface can be easily adjusted by the concentration of DNA probes during immobilization. Furthermore, the probes spatial orientation and structural flexibility are advantageous for more efficient signal response in the proposed assay.

The present method and system will now be illustrated using the non-limiting and exemplary example of the detection of otolin-1 and prestin proteins in blood.

EXAMPLES

In the example of detection of otolin-1, the recognition molecules brought to the surface of the nanostructured electrode include anti-otolin-1 antibody, which is conjugated to streptavidin (ratio 1:1), and further bound to the biotin on the signaling DNA probes through streptavidin-biotin conjugation. However, it will be appreciated that the anti-otolin-1 antibody may be replaced by otolin-1 protein or otolin-1 protein antigen or a peptide-derivate of otolin-1 protein for indirect detection of target otolin-1, for example in a competition assay.

For the detection of prestin proteins in blood, the recognition molecules bound to the surface of the nanostructured electrode include anti-prestin antibody, which is conjugates to streptavidin (ratio 1:1), and further bound to the biotin on the signaling DNA probes through streptavidin-biotin conjugation. The recognition antibody, which is used for direct capturing of target prestin can be replaced with a peptide-derivate of prestin antibody or antibody Fab fragment as long as the affinity of binding is still maintained. On the other hand, the recognition molecule can also be the prestin protein or a peptide-derivate of prestin protein for indirect detection of target prestin, for example in a competition assay.

Materials and Methods

Reagents

Glass chips (Telic; Valenica, CA), HAuCl4 solution (Sigma Aldrich), 6N-hydrochloric acid (HCl; VWR), Tris (2-carboxyethyl) phosphine hydrochloride (TCEP; Sigma-Aldrich), 6-Mercapto-1-hexanol (MCH; Sigma-Aldrich), Phos-phate-buffered saline (PBS, pH 7.4, 1X; Invitrogen), Magnesium chloride (>=98%; Sigma-Aldrich), were all used as received. The DNA constructs (Table 2) synthesized and HPLC purified (Biosearch Technologies Inc., Novato, CA), were aliquoted and stored at −20° C. (degrees Celsius).

TABLE 2

| Sequences of capturing and signaling DNA probes. |
|---|
| Capture strands |
| 5'-HS-(CH2)6-AAGG AAA GGG AAG AAG TTTA CTC CAC GTG CTC |
| Signaling strands |
| 5'-CTT CTT CCC TTT CCTT-MB |

Biotin-conjugated rabbit polyclonal antibody to human otolin-1 and to human SLC26A5 (prestin) (anti-OTOL1 and anti-PRES; LifeSpan Biosciences Inc.); streptavidin (Sigma Aldrich), otolin-1 protein antigen (26 kDa (kiloDal-tons)); Novus Biologicals) were all aliquoted and stored at −20° C. for long-term storage and at 4° C. for short-term use. SLC26A5 or prestin protein (81.4 kDa; Novus Biologicals) was aliquoted and stored at −80° C. Single-donor human whole blood from Innovative Research, that contains heparin as an anticoagu-lant, was aliquoted and frozen at −20° C. prior to use.

Instrumentation

Direct current (DC) potential amperometry and square wave voltammetry (SWV) was carried out by PalmSens4 potentiostat/galvanostat/impedance ana-lyzer combined with MUS08R2 multiplexer. A conventional three-electrode cell was used with a platinum wire counter electrode (CE; Sigma-Aldrich), an Ag/AgCl reference electrode (RE; CH Instruments), and the chip substrate as the working electrode.

On-Chip Electrode Preparation

Glass chips were patterned with the leads and the electrodes at their ter-minals by first precoating with a 5 nm-Cr, coating with a 50 nm-Au, coating with a layer of AZ 1600 positive photoresist, selective exposure to 900 W UV for 12 s, developing in MF 312 for 40 s, and wet etching of Au and Cr on the unpro-tected areas. The 10 μm-apertures were then formed on the electrodes by spincast of the negative photoresist (SU-8 2002) at 4500 revolutions per minute (rpm) for 40 s on the patterned chips, exposing for 12 seconds(s), and then developing for 1 min. Chip substrates with twenty addressable 10-μm-apertures were rinsed with acetone, isopropyl alcohol, and DI water, then dried with the flow of nitrogen.

Chips were immersed in a 3 milliliter (ml) electrolyte solution containing 50 mM $HAuCl_4$ and 0.5 M HCl. Using DC potential amperometry at 0 mV for 200 s (for 200 μm NE1 and NE2) and 100 s (for 100 μm NE3), the gold nanostructured electrodes (NEs) are electrodeposited on the apertures. All the experiments were done at room temperature. The chips were then rinsed with DI water and dried with air blow to become ready for capturing probe-immobilization.

Surface immobilization was done with 100 nM and 200 nM capturing probes in 1×PBS+10 mM $MgCl_2$. Prior to immobilization, 1 μl of 0.1 mM capturing probes were incubated with 2 μl of 10 mM TCEP for 1 h for reduction of disulfide bonds, then diluted in 1×PBS+10 mM $MgCl_2$ to the desired concentrations; 100 μL of capturing probe solutions of 100 nM (on NE1 and NE3) and 200 nM (on NE2) were applied on the individual chips, to cover all over the area of the electrodes and kept overnight. After washing with 1×PBS, 100 μL of 3 mM MCH was put on the electrodes for 3 hr and then washed with 1×PBS. The surface density of the capturing probes was calculated between $1\times10^{12}$–$5\times10^{12}$ $cm^{-2}$ depending on the size of the electrode 41

Electrochemical Measurement

SWV was used to collect the experimental data from −0.45 to 0.05V in increments of 0.001V vs. Ag/AgCI, with an amplitude of 50 mV and a frequency of 60 Hz. Peak currents were fitted using the PSTrace software.

In Buffer Media

The recognition complex was prepared by pre-incubation of antibody with streptavidin (1:1) overnight. Then the signaling probe was added to the mixture (5:1) and (10:1) overnight to make a final recognition solution of 25 nM signaling probe+5 nM streptavidin-conjugated-antibody and 10 nM signaling probe+100 pM streptavidin-conjugated-antibody, respectively.

In human whole blood (>71%): 10 μL of the pre-(overnight) incubated recognition complex solution of 20 nM (described above) is mixed with 1 μL of the 1 μM signaling probe overnight and reached to 40 μL volume by adding whole blood. Proteins were first spiked in whole blood (0.2 μL of protein to 10 μL of whole blood) prior to mixing with the recognition compound.

Figure 3:
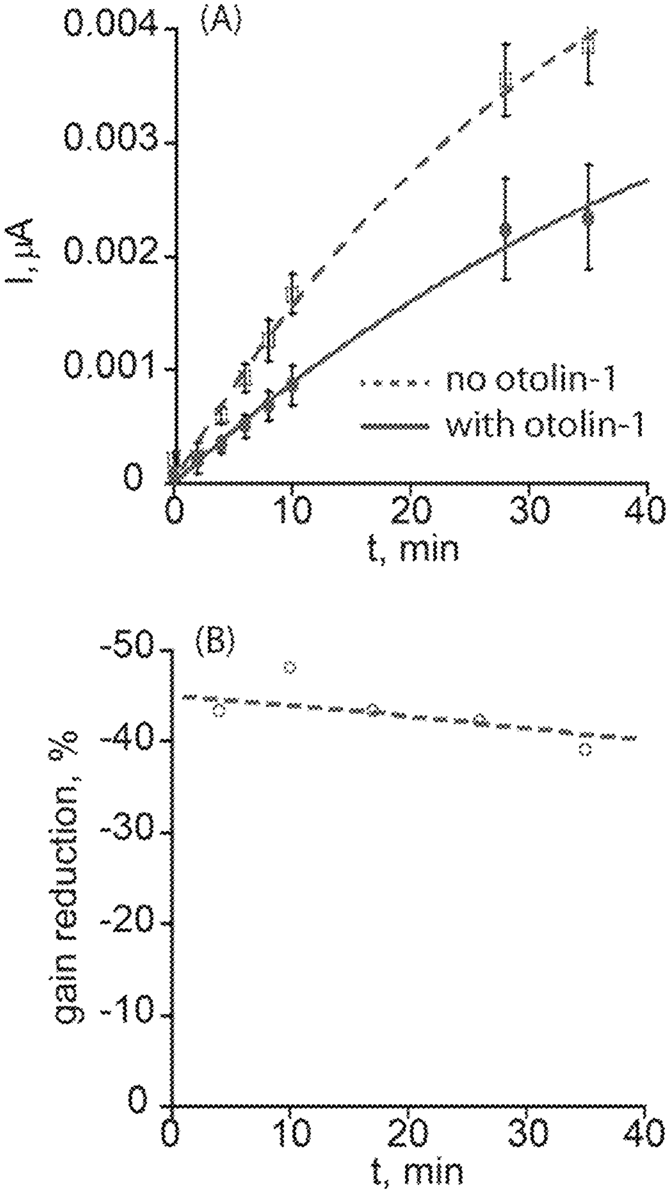
FIG. 3 show assay response-time using kinetics and gain reduction in which panel A shows a plot of current in microamps (μA) versus time (minutes) which shows hybridization kinetics of the signaling probes in the absence and presence of target otolin-1, and panel B is a plot of gain reduction % versus time (minutes) which shows the slight changes in the gain reduction versus time, indicating the maximum performance of the assay was within the first 10 min.

All measurements were taken immediately after 15 min incubation of protein with the mixture of recognition bound to signaling probe solution. For the incubation, the chips were divided into two zones using a hydrophobic pen, each having ten electrodes that were loaded with 10 μL-solution. One of the zones on the chip was always assigned for the control test. After 10 min of acquisition (extracted from FIG. 3), the chips were unloaded and reloaded with 1×PBS or with whole blood (100%) for the signal measurement in buffer media and whole blood, respectively. Results are presented in terms of current (knowing that the geometric area of the electrode is 0.03 $mm^2$ for NE1 and NE2 and 0.008 $mm_2$ for NE3). Control samples (ctrl.) are representing the response to 10 nM of signaling probes after 10 min.

Gain Reduction

This value is calculated as the difference in peak current of the samples with and without the target protein divided by the initial peak current (without target protein).

Binding Curves

Binding curves or dose-response curves were obtained by testing various concentrations of protein on the platform. Individual curves were fitted to a single-site binding mechanism ($C_0$=background current; $C_{50\%}$ is the concentration of target proteins at when the sensor reaches 50% of the signal amplitude:

$$C_{[Target]} = C_0 + \left(\frac{[\text{Target}](\text{current amplitude})}{[\text{Target}] + C_{50\%}}\right)$$

Probe Density Calculations

Capturing probe surface density is defined by the number of moles of capturing probes per unit area of the NE ($N_t$) that is equivalent to the number of methylene blue (MB) molecules being placed on the surface through hybridization:

$$\text{peak current} = 2nfFN_t \frac{\sinh\left(\frac{nFEac}{RT}\right)}{\cosh\left(\frac{nFEac}{RT}\right)+1}$$

n=2: number of electrons transferred per MB label

F: Faraday constant

R: universal gas constant

T: temperature

Eac: amplitude f: frequency of the applied voltage perturbation.

We estimated the capturing probes surface density on three different NEs (based on the size and immobilization concentration) after 10 min of hybridizing to 100 nM signaling probes as presented in Table 3.

TABLE 3

The estimated density of capturing probes.

| | area, $cm^2$ | [probe], nM | density, $1/cm^2$ |
|---|---|---|---|
| NE1 | 0.0003 | 100 | $(1.26 \pm 0.38) \times 10^{12}$ |
| NE2 | 0.0003 | 200 | $(4.57 \pm 0.84) \times 10^{12}$ |
| NE3 | 0.00008 | 100 | $(3.64 \pm 0.56) \times 10^{12}$ |

Statistics

Data for bar charts and binding curves are reported as mean values±standard errors of the means and were analyzed using GraphPad Prism 8.0 (GraphPad Software Inc., San Diego, CA). Data for FIGS. 1C-OTOL1, 2, and 4 were analyzed by one-way analysis of variance (ANOVA) with omnibus statistics presented in Table 4.

TABLE 4

Statistics measured by one-way analysis of variance for otolin-1 and prestin electrochemical immuno-biosensor. Owing to the fact that we performed multiple ANOVA tests (N = 10) for detection of otolin-1 and prestin, we used Bonferroni correction to adjust our alpha criterion to 0.005.

| FIG. | ANOVA table |
|---|---|
| 1C', OTOL1 | F (2, 20) = 23.78; P < 0.0001 |
| 1C", OTOL1 | F (2, 35) = 35.21; P < 0.0001 |
| 2 | F (9, 136) = 52.90; P < 0.0001 |
| 4A, NE1 | F (4, 95) = 38.75; P < 0.0001 |
| 4A, NE2 | F (4, 92) = 70.62; P < 0.0001 |
| 4B | F (3, 68) = 5.253; P = 0.0026 |
| 4C | F (5, 48) = 3.801; P = 0.0056† |
| 4A' | F (4, 91) = 299.3; P < 0.0001 |
| 4B' | F (3, 36) = 20.48; P < 0.0001 |
| 4C' | F (4, 35) = 125.9; P < 0.0001 |

†= not significant.

Post hoc comparisons were done by Tukey's Honest Significant Difference (HSD) test. P-values below the alpha criterion (probability of Type 1 error) of 0.05 were considered statistically significant in all post hoc tests, whereas the alpha criterion for one-way ANOVA tests (described in Table 4) were Bonferroni-corrected due to multiple testing. For the data in FIG. 1C-PRES, the inde-pendent t-tests were done for the analysis with statistics presented in Table 5.

TABLE 5

Statistics measured by independent t-tests for prestin electrochemical immuno-biosensor.

| FIG. | target prestin |
|---|---|
| 1C', PRES | t(15) = 7.235; P < 0.0001 |
| 1C", PRES | t(32) = 45.70; P < 0.0001 |

Figure 1B:
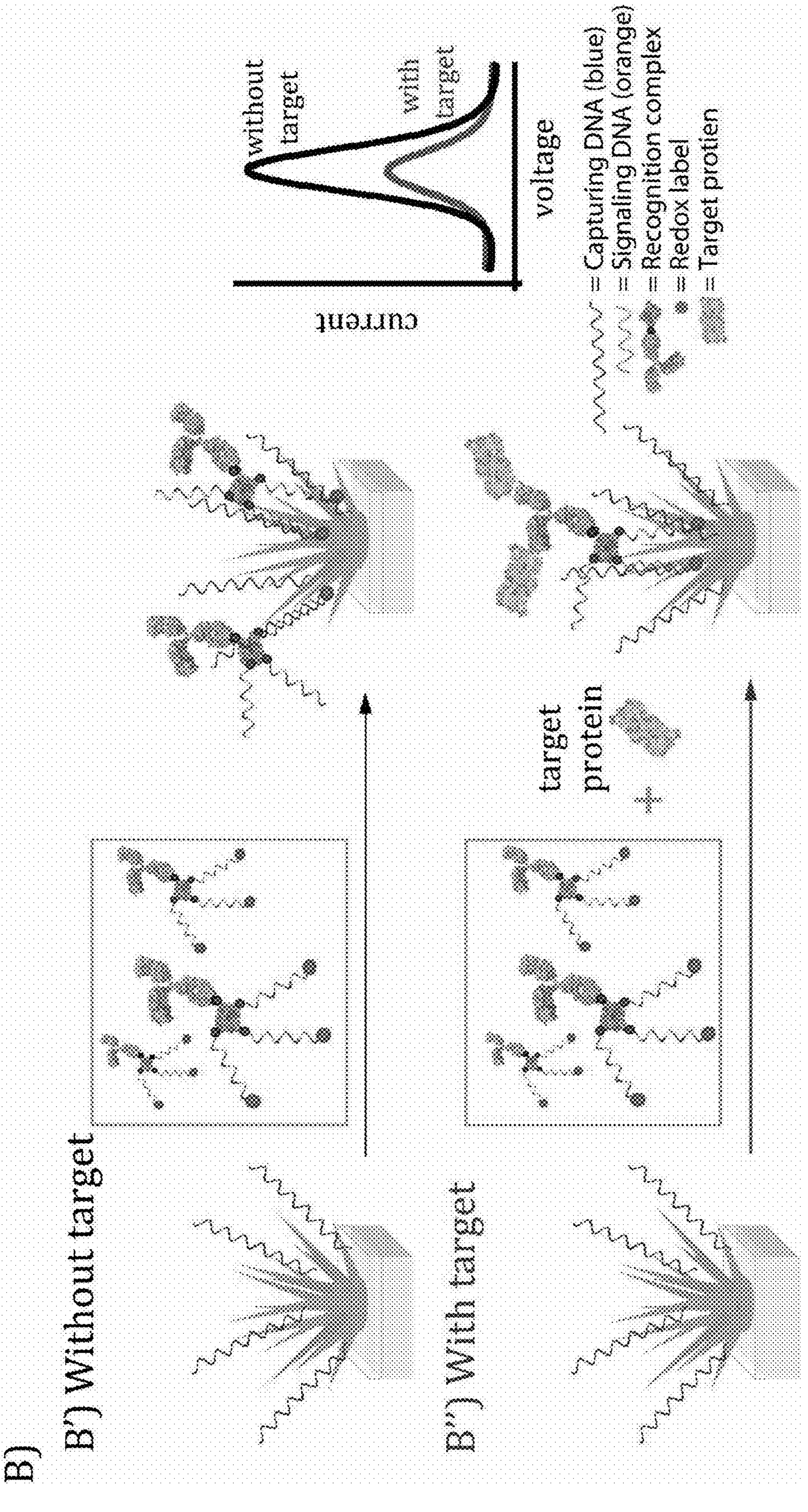
Figure 1C:
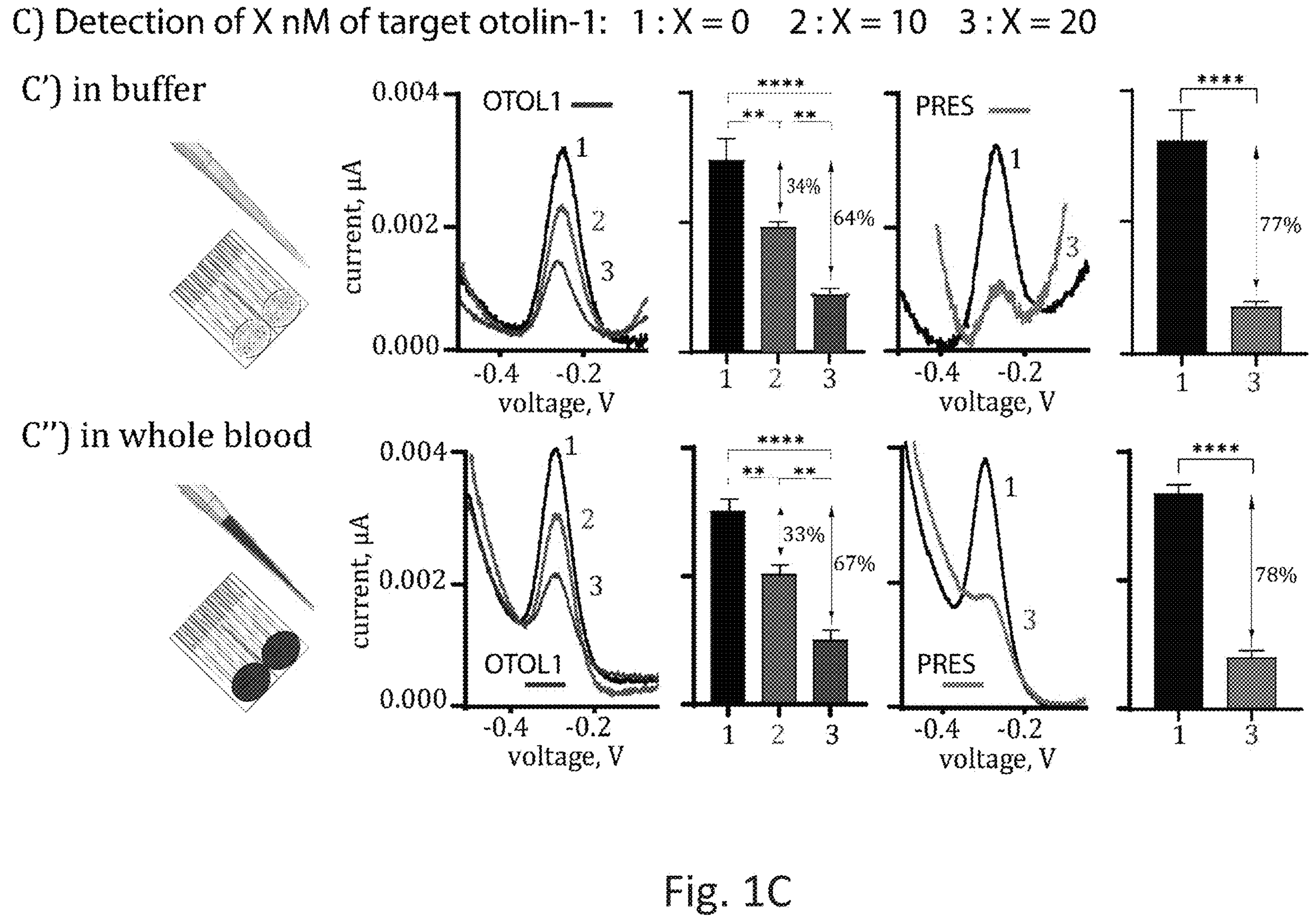

Disclosed herein is a single-step assay taking advantage of the specificity of interactions of oligonucleotide sequences in the sensor's signal, even when deployed in complex media 4749 (see FIGS. 1A to 1C). Nanostructures are electrodeposited with high curvature, as working electrodes (NEs) on the 10 μm-apertures of a glass chip with twenty addressable leads (see FIG. 1A). The nanostructuring of the surface provides tunable sensitivities and linear detection ranges for the electrochemical detection platform. Short single-strand capturing DNA probes (longer strands) are immobilized on the gold nanostructures (see panel 1B of FIG. 1B). The signaling DNA probes (shorter strands) are shorter and complementary to the capturing strands, which upon hybridization, can bring the redox moiety, methylene blue (MB), to the surface and generate a current signal (see panel 1B' of FIG. 1B, top row). On the other extremity, the signaling probes carry the recognition element utilizing a streptavidin-biotin interaction. This can apply steric effects on surface hybridization, which can be diminished within the curvatures of the nanostructured surface. When the target protein is bound to the recognition element on the signaling DNA probe (see panel 1B" of FIG. 1B, bottom row), steric hindrance is increased, limiting the number of successful hybridizations to the surface resulting in a reduction in the current signal (with-target curve vs. without-target curve).

Detection of Otolin-1 and Prestin

The mammalian inner ear contains proteins that circulate in the blood-stream. Otolin-1, a glycoprotein expressed within the vestibular supporting cells, provides a scaffold for otoconia on the sensory epithelia maintaining the body balance[24]. Prestin is a motor protein in the outer hair cells and operates to elongate the cells in support of normal hearing sensitivity[50]. As proof of principle to our DNA-based immunoassay, we targeted the protein detection (here, a 26-kDa otolin-1 antigen and an 81-kDa prestin) in the buffer (see panel 1C' of FIG. 1C) as well as in whole blood (see panel 1C" of FIG. 1C). To do so, we first designed a recognition element by having their antibodies (anti-otolin-1 and anti-prestin) attached to the signaling probes via streptavidin-biotin conjugation (see FIG. 1B).

Then the sensor platform was developed to maintain the steric hindrance of the target protein despite the potential steric effects of other components of the assay (e.g., the antibody, streptavidin, or the DNA probes). The incorporation of synthetic DNA probes, combined with the anti-protein specific antibody, regulates the capturing and detection of protein without any interference from the non-specific interactions when deployed in whole blood. This is evident by comparing the signal gain reductions of otolin-1 (OTOL1) in the buffer (34% and 64%) and whole blood (33% and 67%) at 10 nM and 20 nM protein concentrations. The detection of prestin (PRES) at 20 nM, further proved the similarity of the sensor's response in the buffer (77%) and whole blood (78%). The increase in the signal gain of prestin compared to otolin-1 (78% vs. 67%) could be attributed to the difference in the size of the target proteins (26 kDa vs. 81 kDa). Furthermore, increasing the concentration of protein (10 nM to 20 nM) resulted in more signal loss (33% vs. 67%), representing the quantitative ability of the sensor even in whole blood.

Immunoassay Design and Validation for Otolin-1 and Prestin.

Surface immobilization was done on nanostructures via sulfur-gold bonds, at a high surface density of the capturing probes, followed by back-filling with the 6-mercaptohexanol (MCH). We used a thiol-modified (on the 5' end) 32-base DNA construct, as the capturing probe on the electrode's surface. The current response of such a surface represents no peak (FIG. 2-(1,1', and 1")). Signaling probes were designed to be 16-base long with a biotin on the 5' end and a methylene blue (MB) on the 3' end, complementary to the lower half of the capturing probe construct. Upon hybridization to the high-density of capturing probes on the NEs, a relatively high peak current was measured as the MB is placed on the electrode surface resulting in a successful electron transfer (FIG. 2-(2, 2', and 2")). The response peak was not affected by the presence of otolin-1 (OTOL1) and prestin (PRES) proteins (3, 3' and 3") or antibodies (4, 4', and 4").

Figure 2:
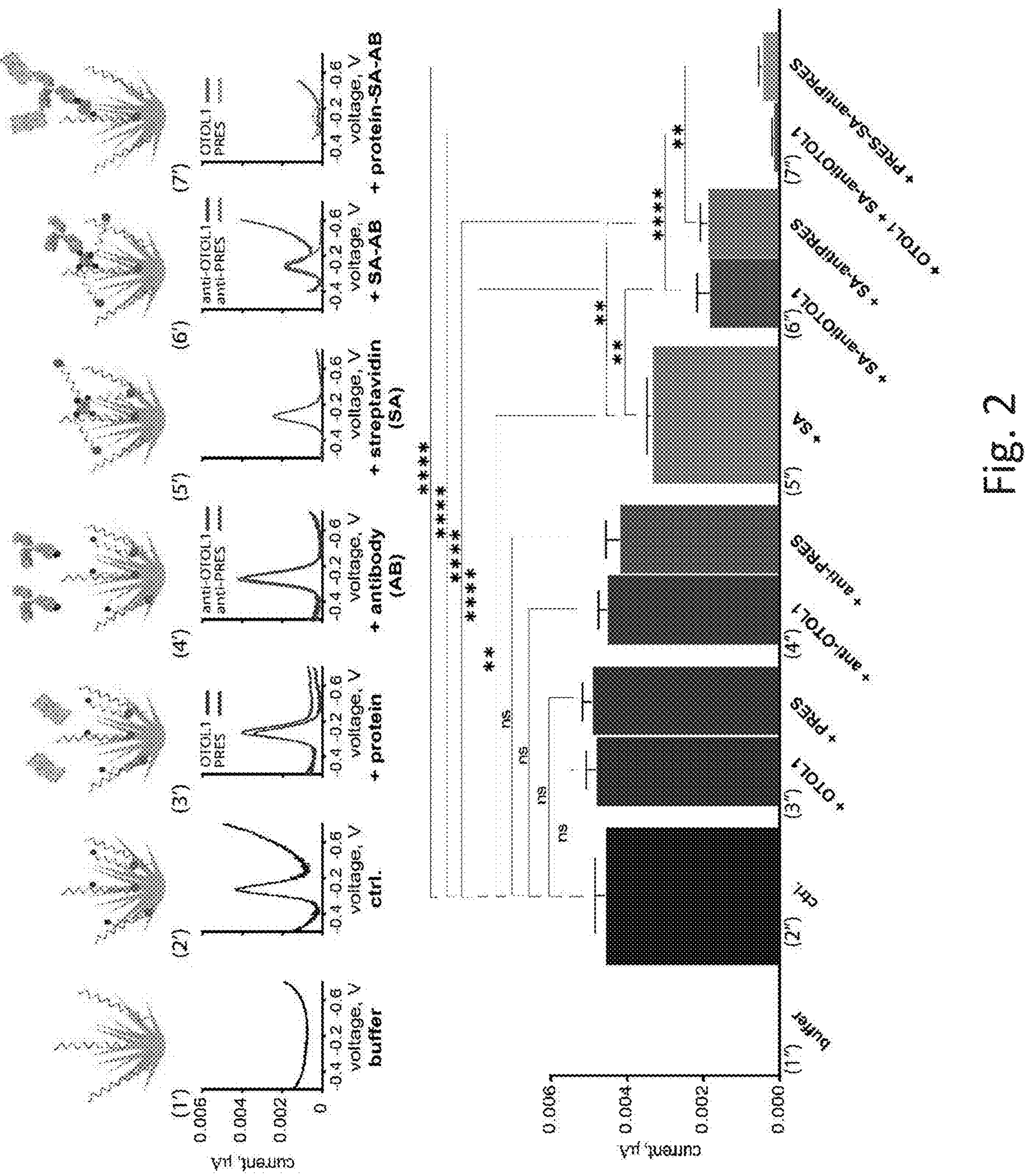
FIG. 2 shows steric-based assay validation for the detection of otolin-1 and prestin. Assay illustration, square wave voltammetry responses, and the resulting current signal of the immobilized nanostructured electrodes reported, (1,1', 1") in buffer, then in signaling probes (2, 2',2") alone, (3, 3', 3") with otolin-1 (OTOL1) or prestin (PRES), (4, 4', 4") with otolin-1 antibody (anti-OTOL1) or prestin antibody (anti-PRES), (5, 5', 5") with streptavidin (SA), and signaling probes with recognition elements of SA-antiOTOL1 and SA-antiPRES (6, 6', 6")in the absence of target, and (7, 7', 7") in the presence of target. ctrl.: control/signaling probes; 10 nM signaling probes, 100 pM recognition element (1:1 SA: antibody), 500 pM otolin-1 and 500 pM prestin protein; buffer media: PBS (Phosphate-buffered saline) 1×10 mM (millimolar) $MgCl_2$. ** P<0.0001, * P<0.001, *P<0.05, and ns: non-significant versus different concentrations.

However, once the signaling probes were introduced to the streptavidin (55 kDa) (FIG. 2-(5, 5', and 5")), or the streptavidin-conjugated antibodies (210 kDa (kilodaltons)) (FIG. 2-(6, 6', and 6")), the current signal decreased by 25% and ~60% (SA-anti-OTOL1, 62% and SA-anti-PRES, 58%), respectively. This is due to the interactions between streptavidin and biotin on signaling probes, and consequently, the steric hindrance of attached molecules on the surface hybridization.

A further signal decrease occurred when the recognition molecule was attached to the target proteins (otolin-1 antigen: 26 kDa and prestin: 81 kDa), resulting in elevated steric hindrance effect of a bigger molecular compound (OTOL1 compound, 262 kDa and PRES compound, 372 kDa) on the surface hybridization (FIGS. 2-(7, 7', and 7").

The signal suppression within this assay originated from, first, the smaller number of signaling probes reaching the surface due to the steric hindrance of attached macromolecules, and second, their lower rate of hybridization[51]. We studied the hybridization kinetics of signaling probes carrying the recognition element in the absence and presence of the target otolin-1 (FIG. 3A). The calculated rate and time of hybridization (Table 1) indicated that there was a slight delay in hybridization to the surface in the presence of the target. We then measured the increase in the signal gain reduction of the sensor versus time, which shows a gradual decrease after the first minutes. This implies that the maximum performance of the assay can be achieved within the first 10 min (FIG. 3B).

TABLE 1

The hybridization kinetics and the consequent rate and time of hybridization.

| | k, $min^{-1}$ | $t_{1/2}$, min |
|---|---|---|
| no target | 0.03 | 23 |
| with target | 0.02 | 37 |

Immunoassay Optimization

Figure 4:
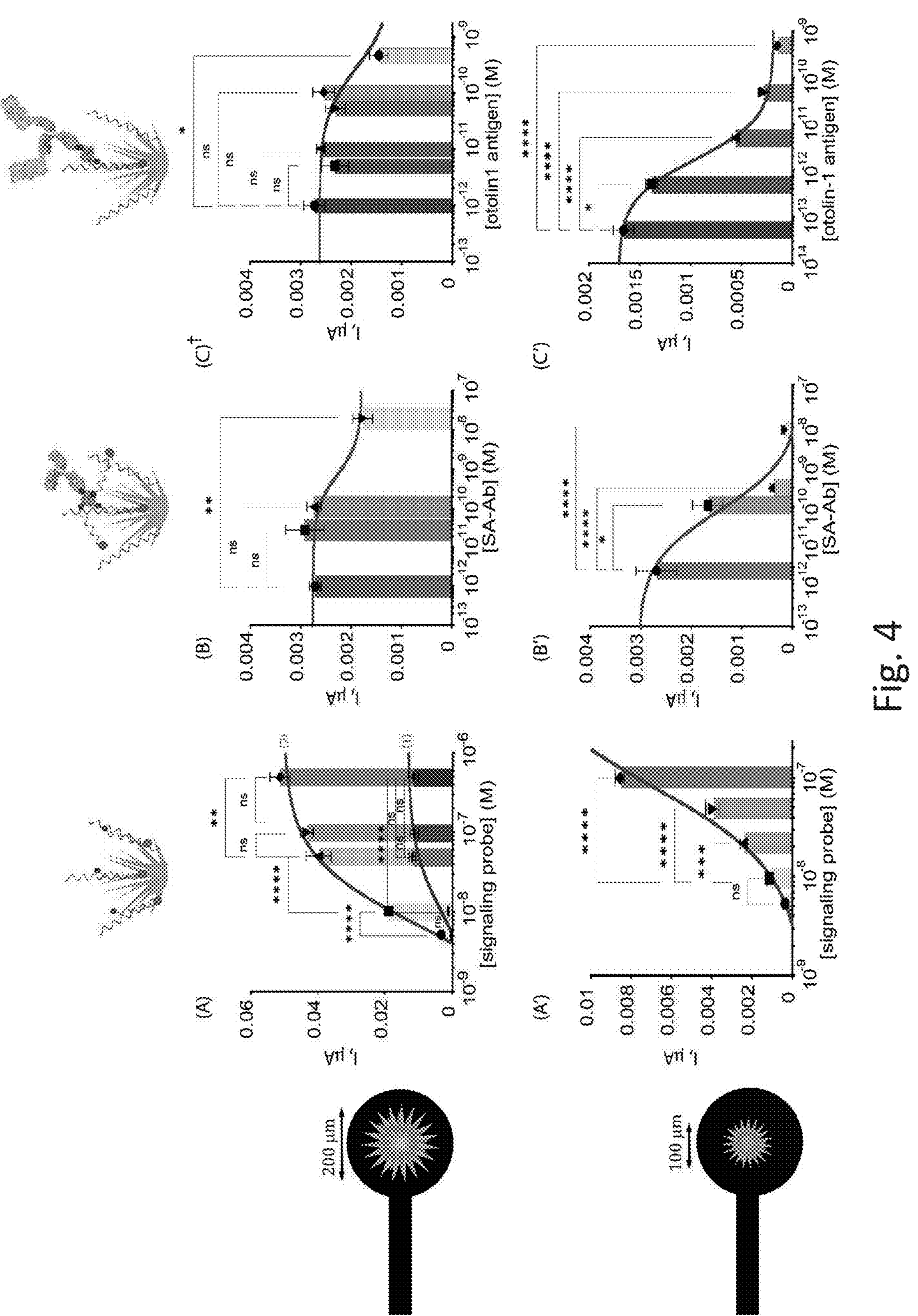
FIG. 4 Optimization of the assay through dose-response curves. Comparison of dose-response curves on NE1, NE2, NE3 when applied in signaling probes (A, A') without recognition element have $C_{50\%,\ A,NE1}$=16±3 nM, $C_{50\%,\ A,\ NE2}$=10±3 nM, and $C_{50\%,\ A',NE3}$=85±13 nM, and (B, B') with recognition element in the absence of protein have $C_{50\%,\ B,NE1}$=750 nM and $C_{50\%,\ B',\ NE3}$=85 nM, and (C, C') with recognition element in the presence of protein have $C_{50\%,\ C,\ NE1}$=280 pM and $C_{50\%,\ C',\ NE3}$=2 pM. NEs1 to 3 are introduced in Table 3;** P<0.0001, * P<0.001, *P<0.05, and ns: non-significant versus different concentrations. †Although the ANOVA model for panel 4C was not significant, at the highest level of the Otolin1 antigen (500 pM), the reduction in the response was at the start of the dose-response curve and was significantly reduced (*P<0.05).

The maximum surface density of capturing probes combined with the optimum size of the electrode is required to differentiate the signal of the target protein from the background signal (steric hindrance of the conjugated antibody with and without target protein). Then, the minimum amount of signaling probes required to saturate the surface hybridization, and the minimum amount required to generate a measurable signal, can be deducted from the dose-response curves on three NEs with variations in size and immobilized-capturing probe concentration-NE1 (200 μm, 100 nM), NE2 (200 μm, 200 nM) and NE3 (100 μm, 100 nM) (FIGS. 4A, 4A'). We used tree-like nanostructures that possess high-curvatures to ensure the high-surface density of capturing probes as well as the high density of hybridization to the surface[39]. In this case, we showed that when the immobilization concentration is adjusted to 100 nM, and the concentration of the signaling probe to 10 nM, we could maintain the high current signal as well as we could minimize the background current induced by the large (210 kDa) recognition element.

The inventors estimated the minimum amount of recognition molecule required to maintain the steric hindrance of the target molecule once it was attached to the signaling probe, as well as a high current signal in the absence of the target molecule. The dose-response curves of the recognition molecules were measured with 10 nM of signaling probes (deducted from $C_{50\%}$ of FIGS. 4As) on the NEs (FIGS. 4B, 4B'; $C_{50\%,\ NE1}$=750 PM and $C_{50\%,\ NE3}$=85 PM) implying that the smaller NEs (NE3) were capable of complete suppression of the background current. With an optimum amount of recognition element (data is shown for 100 pM), we then conducted the binding curve of target protein (here, otolin-1; FIGS. 4C, 4C'). The resulting $C_{50\%}$ was measured at 280 pM on NE1 and 2 pM on NE3. We showed that with the NE3, we could achieve low picomolar concentrations of the protein within a three-fold quantitative range within less than 10 min, implying not only the impact of electrode's dimension on the successful reduction of the detection limit but also the capacity of this technique for rapid point-of-care detection of proteins.

DISCUSSION

Using the idea of steric hindrance on nanostructured surfaces that could alter the hybridization of DNA probes to their complementary strands on the surface generating a measurable linear range, the present inventors have created the first biosensor for electrochemical detection of otolin-1 and prestin, two circulating biomarkers of the mammalian inner ear. Compared with the complicated multiple-step ELISA-based approaches that are used as the gold standard for the detection of inner ear proteins, the approach disclosed herein has the advantage of simplicity, rapidity together with the specificity of the signal, making it a strong candidate for the point-of-care diagnostic platforms for inner ear diseases. Although this disclosure has been illustrated with respect to the detection of two inner ear proteins, otolin-1 and prestin, it can be adapted for other inner ear biomarkers as well as well as for any other circulating protein biomarkers.

The DNA-based detection platform disclosed herein incorporates a recognition strategy with an antibody conjugated to streptavidin for the detection of proteins at low concentrations. In this case, a combination of the high density of capturing DNA probes on the surface, and an optimal density of signaling complementary DNA probes carrying the streptavidin-antibody recognition element to the surface was calculated to ensure the best performance of the assay on the nanostructured electrodes for quantitative detection of protein. The inventors have shown that by using small-scale nanostructured electrodes, they can significantly improve the sensitivity down to low picomolar concentrations with a three-fold linear detection range. The inventors have also demonstrated the assay detection time in less than ten minutes, indicating that the assay can be utilized for rapid diagnostic techniques.

The physiological levels of otolin-1 and prestin in human blood are in the femtomolar ranges. Their variations start from around 100 μg/ml in healthy individuals by factors of 50 to 100 μg/ml up to about 1000 μg/ml depending on the age and level of damage[19,24,52]. However, quantitative measurements within whole blood can be challenging, mainly when detecting low physiological levels, such as for the inner ear proteins[40]. The inventors have provided a strategy to reduce the detection limit and yet maintain the linearity of the sensor by lowering the electrode's dimension while enabling the high curvatures of nanostructuring. The combination of synthetic assays with nanostructured electrodes can also be improved to promote the rate of reactions and can be adapted within a microfluidic device to accelerate the rate of target delivery and eventually to develop a rapid test platform in therapeutic ranges.

The present disclosure advantageously provides a new non-invasive diagnostic approach for inner ear diseases that is capable of rapid detection of blood-circulating biomarkers through a point-of-care biosensor platform. The present method and system has been illustrated with respect to a method and system for the single-step detection of otolin-1 and prestin protein but it will be appreciated that the present method and sensor platform made be applied to the detection of other unique and promising biomarkers of the inner ear, includeing the circulating DNAs/RNAs (ribonucleic acids), proteins, metabolites, cells, exosomes, and small molecules, in order to develop a comprehensive multiplexing device for the point-of-care diagnosis of inner ear disorders.

Ultimately, more accurate diagnostics will help identify the sites of damage in the inner ear or central auditory pathway and will provide the ability to monitor the occurrence and progression of a variety of inner ear disorders as well as the efficacy of treatment. Furthermore, while the initial design of the point-of-care biosensing platform is for the detection of inner ear protein biomarkers, several clinically relevant circumstances, e.g., infectious or autoimmune diseases would benefit from such an approach for the rapid early-stage diagnosis.

It will be appreciated that while the present electrochemical immuno-bio-sensor-based method and system has been illustrated with respect to the detection of otolin-1 and prestin proteins, it will be appreciated that this method and system can be adapted for all diseased characterized by circulating protein biomarkers, including for example cancers, infectious and autoimmune diseases, as well as, any other acute and chronic illnesses. For each disease that the system is to be configured to detect, the method involves determining the circulating protein to be detected, The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES (1) Laksanasopin, T.; Guo, T. W.; Nayak, S.; Sridhara, A. A.; Xie, S.; Olowookere, O. O.; Cadinu, P.; Meng, F.; Chee, N. H.; Kim, *J. Science translational medicine* 2015, 7, 273re271-273re271.

(2) Pang, Y.; Wang, C.; Lu, L.; Wang, C.; Sun, Z.; Xiao, R. *Biosensors and Bioelectronics* 2019, 130, 204-213.

(3) Mattox, A. K.; Bettegowda, C.; Zhou, S.; Papadopoulos, N.; Kinzler, K. W.; Vogelstein, B. *Science translational medicine* 2019, 11, eaayl984.

(4) Wei, T.-Y.; Fu, Y.; Chang, K.-H.; Lin, K.-J.; Lu, Y.-J.; Cheng, C.-M. *Trends in biotechnology* 2018, 36, 290-303.

(5) Moon, J.-M.; Thapliyal, N.; Hussain, K. K.; Goyal, R. N.; Shim, Y.-B. *Biosensors and Bioelectronics* 2018, 102, 540-552.

(6) Stapells, D. R.; Oates, P. *Audiology and Neurotology* 1997, 2, 257-280.

(7) Rosengren, S.; Welgampola, M.; Colebatch, *J. Clinical neurophysiology* 2010, 121, 636-651.

(8) Visser, J. E.; Carpenter, M. G.; van der Kooij, H.; Bloem, B. R. *Clinical Neurophysiology* 2008, 119, 2424-2436.

(9) Landegger, L. D.; Psaltis, D.; Stankovic, K. M. *Hearing research* 2016, 335, 83-93.

(10) Liberman, M. C.; Epstein, M. J.; Cleveland, S. S.; Wang, H.; Maison, S. F. *PloS one* 2016, 11, e0162726.

(11) Moser, T.; Starr, A. *Nature Reviews Neurology* 2016, 12, 135-149.

(12) Taiber, S.; Avraham, K. B. *Neuroscience letters* 2019, 134527.

(13) Nacher-Soler, G.; Garrido, J. M.; Rodríguez-Serrano, F. *Archives of medical science: AMS* 2019, 15, 957.

(14) Omichi, R.; Shibata, S. B.; Morton, C. C.; Smith, R. J. *Human molecular genetics* 2019, 28, R65-R79.

(15) Meas, S. J.; Zhang, C.-L.; Dabdoub, A. Frontiers in Molecular *Neuroscience* 2018, 11.

(16) Samarajeewa, A.; Jacques, B. E.; Dabdoub, A. *Molecular Therapy* 2019.

(17) Naples, J.; Cox, R.; Bonaiuto, G.; Parham, K. *Otolaryngology-Head and Neck Surgery* 2018, 158, 541-546.

(18) Hana, R. S.; Bawi, B. L. *Ibnosina Journal of Medicine and Biomedical Sciences* 2018, 10, 60.

(19) Doğan, M.; Şahin, M.; Kurtulmuş, Y. *The journal of international advanced otology* 2019, 15, 200.

(20) Avallone, E.; Schmitt, H.; Lilli, G.; Warnecke, A.; Lesinski-Schiedat, A.; Lenarz, T.; Willenborg, K. *Laryngo-Rhino-Otologie* 2018, 97, 10428.

(21) Deans, M. R.; Peterson, J. M.; Wong, G. W. *PloS one* 2010, 5, e12765.

(22) Mio, K.; Kubo, Y.; Ogura, T.; Yamamoto, T.; Arisaka, F.; Sato, C. *Journal of Biological Chemistry* 2008, 283, 1137-1145.

(23) Dallos, P.; Fakler, B. *Nature Reviews Molecular Cell Biology* 2002, 3, 104-111.

(24) Parham, K.; Sacks, D.; Bixby, C.; Fall, P. *Otolaryngology-Head and Neck Surgery* 2014, 151, 1038-1040.

(25) Parham, K.; Dyhrfjeld-Johnsen, J. *Otology & Neurotology* 2016, 37, 1217-1222.

(26) Engvall, E.; Perlmann, *P. Immunochemistry* 1971, 8, 871-874.

(27) Towbin, H.; Staehelin, T.; Gordon, J. *Proceedings of the National Academy of Sciences* 1979, 76, 4350-4354.

(28) Budhathoki-Uprety, J.; Shah, J.; Korsen, J. A.; Wayne, A. E.; Galassi, T. V.; Cohen, J. R.; Harvey, J. D.; Jena, P. V.; Ramanathan, L. V.; Jaimes, E. A.; Heller, D. A. *Nature Communications* 2019, 10, 3605.

(29) Hassan, U.; Ghonge, T.; Reddy Jr, B.; Patel, M.; Rappleye, M.; Taneja, I.; Tanna, A.; Healey, R.; Manusry, N.; Price, Z.; Jensen, T.; Berger, J.; Hasnain, A.; Flaugher, E.; Liu, S.; Davis, B.; Kumar, J.; White, K.; Bashir, R. *Nature Communications* 2017, 8, 15949.

(30) Chinnadayyala, S. R.; Park, J.; Le, H. T. N.; Santhosh, M.; Kadam, A. N.; Cho, S. *Biosensors and Bioelectronics* 2019, 126, 68-81.

(31) Labib, M.; Sargent, E. H.; Kelley, S. O. *Chemical reviews* 2016, 116, 9001-9090.

(32) Chen, L.-C.; Wang, E.; Tai, C.-S.; Chiu, Y.-C.; Li, C.-W.; Lin, Y.-R.; Lee, T.-H.; Huang, C.-W.; Chen, J.-C.; Chen, W. L. *Biosensors and Bioelectronics* 2020, 155, 112111.

(33) Chambers, J. P.; Arulanandam, B. P.; Matta, L. L.; Weis, A.; Valdes, J. J. *Current Issues in Molecular Biology* 2008, 10, 1-12.

(34) Ricci, F.; Adornetto, G.; Palleschi, G. *Electrochimica Acta* 2012, 84, 74-83.

(35) Mahshid, S. S.; Mahshid, S.; Vallée-Bélisle, A.; Kelley, S. O. *Analytical chemistry* 2019, 91, 4943-4947.

(36) Mahshid, S. S.; Ricci, F.; Kelley, S. O.; Vallée-Bélisle, A. *ACS Sensors* 2017, 2, 718-723.

(37) Lin, M.; Song, P.; Zhou, G.; Zuo, X.; Aldalbahi, A.; Lou, X.; Shi, J.; Fan, C. *nature protocols* 2016, 11, 1244-1263.

(38) Mahshid, S.; Mepham, A. H.; Mahshid, S. S.; Burgess, I. B.; Saberi Safaei, T.; Sargent, E. H.; Kelley, S. O. *The Journal of Physical Chemistry C* 2016, 120, 21123-21132.

(39) De Luna, P.; Mahshid, S. S.; Das, J.; Luan, B.; Sargent, E. H.; Kelley, S. O.; Zhou, R. *Nano Letters* 2017, 17, 1289-1295.

(40) Kelley, S. O.; Mirkin, C. A.; Walt, D. R.; Ismagilov, R. F.; Toner, M.; Sargent, E. H. *Nature nanotechnology* 2014, 9, 969.

(41) Mahshid, S. S.; Camire, S.; Ricci, F.; Vallee-Belisle, A. *Journal of the American Chemical Society* 2015, 137, 15596-15599.

(42) Mahshid, S. S.; Vallée-Belisle, A.; Kelley, S. O. *Analytical chemistry* 2017, 89, 9751-9757.

(43) Velusamy, V.; Arshak, K.; Yang, C. F.; Yu, L.; Korostynska, O.; Adley, C. *American Journal of Analytical Chemistry* 2011, 2, 392.

(44) Yamaguchi, S.; Shimomura, T.; Tatsuma, T.; Oyama, N. *Analytical chemistry* 1993, 65, 1925-1927.
(45) Ligaj, M.; Jasnowska, J.; Musiał, W. G.; Filipiak, M. *Electrochimica acta* 2006, 51, 5193-5198.
(46) Bonanni, A.; Pividori, M.; Del Valle, M. *Analytical and bioanalytical chemistry* 2007, 389, 851-861.
(47) Zhai, J.; Cui, H.; Yang, R. *Biotechnology advances* 1997, 15, 43-58.
(48) Song, S.; Wang, L.; Li, J.; Fan, C.; Zhao, J. *TrAC Trends in Analytical Chemistry* 2008, 27, 108-117.
(49) Drummond, T. G.; Hill, M. G.; Barton, J. K. *Nature biotechnology* 2003, 21, 1192.
(50) Liberman, M. C.; Gao, J.; He, D. Z.; Wu, X.; Jia, S.; Zuo, *J. Nature* 2002, 419, 300.
(51) Mahshid, S. S.; Vallée-Bólisle, A.; Kelley, S. O. *Analytical chemistry* 2017, 89, 9751-9757.
(52) Tabtabai, R.; Haynes, L.; Kuchel, G. A.; Parham, K. *Otology & neurotology: official publication of the American Otological Society, American Neurotology Society [and] European Academy of Otology and Neurotology* 2017, 38, 865.

Therefore what is claimed is:

1. An electrochemical immuno-biosensor-based method for detecting a target protein in a complex medium, the method comprising the steps of:

selecting the target protein to be detected in the complex medium and providing a sample obtained from a subject, the target protein being an endogenous/circulating protein in the sample;

selecting an antibody complementary to the selected target protein;

preparing a recognition complex comprising the selected antibody, a fragment or a derivative thereof and at least one signaling DNA probe, each said at least one signaling DNA probe having a first end attached to the selected antibody, the fragment or the derivative thereof and a redox moiety covalently attached proximate to a second end of the at least one signaling DNA probe;

mixing the sample of the complex medium with the recognition complex, such that, when present in the sample, the target protein binds with the antibody, the fragment or the derivative thereof of the recognition complex to form a signaling DNA-antibody-antigen complex, and when absent, the antibody, the fragment or the derivative thereof of the recognition complex remains free of the target protein;

contacting the sample with an electrode comprising a high-curvature gold surface having a plurality of capturing DNA probes covalently attached to the gold surface at a first end, each said plurality of capturing DNA probes being longer than the at least one signaling DNA probe and comprising a sequence portion complementary toa sequence portion of the at least one signaling DNA probe, whereby the at least one signaling DNA probe of the recognition complex are capable of hybridizing with the plurality of capturing DNA probes to bring the redox moiety into proximity with the gold surface and generate an electrochemical current upon application of a voltage;

an optimization step in which a surface density of the plurality of capturing DNA probes on the high-curvature gold surface and a dimension and/or curvature of the high-curvature gold surface are selected based on dose-response measurements obtained (i) with the at least one signaling DNA probe in the absence of the antibody, the fragment or the derivative thereof, (ii) with the antibody, the fragment or the derivative thereof present and the target protein absent, and (iii) with the antibody, the fragment or the derivative thereof present and the target protein present, thereby maximizing the current in the absence of the target protein and minimizing background attributable to steric hindrance of the antibody, the fragment or the derivative thereof, and achieving saturated surface hybridization at a minimum signaling DNA probe amount with a reduced effective concentration for target detection within a rapid assay time; and measuring the generated electrochemical current, wherein binding of the target protein to the antibody, the fragment or the derivative thereof of the recognition complex increases steric hindrance reducing hybridization of the at least one signaling DNA probe with the plurality of capturing DNA probes on the gold surface, thereby reducing the generated electrochemical current relative to the current obtained in the absence of the target protein.

2. The method according to claim 1, wherein the dose-response measurements are evaluated using a half-maximal response concentration ($C_{50}$%) criterion across the measurement conditions (i) with the at least one signaling DNA probe in the absence of the antibody, the fragment or the derivative thereof, (ii) with the antibody, the fragment or the derivative thereof present and the target protein absent, and (iii) with the antibody, the fragment or the derivative thereof present and the target protein present.

3. The method according to claim 1, wherein the minimum signaling DNA probe amount corresponds to a concentration sufficient to saturate surface hybridization, as indicated by a dose-response plateau in the condition (i) with the at least one signaling DNA probe in the absence of the antibody, the fragment or the derivative thereof.

4. The method according to claim 1, wherein the selected dimension and/or curvature of the high-curvature gold surface is effective to suppress background current in the condition (ii) with the antibody, the fragment or the derivative thereof present and the target protein absent relative to the condition (i) with the at least one signaling DNA probe in the absence of the antibody, the fragment or the derivative thereof.

5. The method according to claim 1, wherein the high-curvature gold surface comprises tree-like, spiky, or brush-like nanostructures configured to increase capture-probe surface density relative to a flat gold surface.

6. The method of claim 1, wherein the capturing DNA probe immobilization concentration is about 100 nM and the signaling DNA probe concentration is about 10 nM during the dose-response measurements with the at least one signaling DNA probe in the absence of the antibody, the fragment or the derivative thereof.

7. The method of claim 1, wherein the optimization selects a smaller-dimension high-curvature electrode that is effective to reduce background current when the antibody, the fragment or the derivative thereof is attached to the at least one signaling DNA probe and the target protein is absent, and to lower a $C_{50}$% for target detection when the antibody, the fragment or the derivative thereof is attached to the at least one signaling DNA probe and the target protein is present, relative to a larger-dimension high-curvature electrode.

8. The method of claim 1, wherein the optimization yields low-picomolar target detection within a time of less than about 10 minutes from contacting the electrode to measuring the electrochemical current.

9. The method according to claim 1, wherein the antibody, the fragment or the derivative thereof is an antibody.

10. The method according to claim 1, wherein the step of preparing the recognition complex comprise the step of binding the selected antibody, the fragment or the derivative thereof to streptavidin, the ratio of the selected antibody, the fragment or the derivative thereof: streptavidin being 1:1 and attaching each of the at least one signaling DNA probe to the streptavidin via a streptavidin-biotin conjugation, each of the at least one signaling DNA probe having a biotin covalently attached near the first end of the signaling DNA probe.

11. The method according to claim 10, wherein the at least one signaling DNA probe attached to the selected antibody, the fragment or the derivative thereof is three signaling DNA probes.

12. The method of claim 1, wherein measuring the generated electrochemical current comprises performing square-wave voltammetry (SWV) on the sample to obtain a sample current-versus-voltage plot, comparing the sample current-versus-voltage plot to a calibration current-versus-voltage plot obtained from a calibration solution lacking the target protein, and determining the presence or absence of the target protein based on differences between the sample and calibration plots.

13. The method according to claim 1, wherein the redox moiety is an organic or inorganic molecule attachable to the at least one signaling DNA probe and which is capable of generating a redox activity upon the application of the voltage.

14. The method according to claim 1, wherein the complex medium is an animal biofluid selected from the group consisting of whole blood, serum, plasma, saliva, nasopharyngeal, urine, and perilymph.

15. The method according to claim 1, wherein the complex medium is whole blood and the selected target protein is a blood circulating protein.

16. The method according to claim 15, wherein the selected target protein is a protein used as a biomarker for an inner ear-related disease.

17. The method according to claim 16, wherein the selected target protein is otolin-1, and wherein the antibody is an anti-otolin-1 antibody.

18. The method according to claim 16, wherein the selected target protein is prestin, and wherein the antibody is an anti-prestin antibody.

19. The method according to claim 1, wherein a surface density of the plurality of capturing DNA probes covalently attached to the gold surface is between about $1\times10^{12}$ to about $5\times10^{12}$ $cm^{-2}$.

* * * * *